United States Patent
Fonfe et al.

(10) Patent No.: US 9,809,535 B2
(45) Date of Patent: Nov. 7, 2017

(54) PROCESS FOR THE PREPARATION OF ALKYL MERCAPTANS

(71) Applicants: Benjamin Fonfe, Frankfurt (DE);
Stephan Kretz, Biebergemuend (DE);
Harald Jakob, Hasselroth (DE)

(72) Inventors: Benjamin Fonfe, Frankfurt (DE);
Stephan Kretz, Biebergemuend (DE);
Harald Jakob, Hasselroth (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/974,625

(22) Filed: Dec. 18, 2015

(65) Prior Publication Data

US 2016/0176808 A1    Jun. 23, 2016

(30) Foreign Application Priority Data

Dec. 19, 2014  (EP) .................................... 14199311

(51) Int. Cl.
*C07C 319/08*  (2006.01)

(52) U.S. Cl.
CPC ................................. *C07C 319/08* (2013.01)

(58) Field of Classification Search
CPC .................................................. C07C 319/08
See application file for complete search history.

(56) References Cited

U.S. PATENT DOCUMENTS

| | | | |
|---|---|---|---|
| 2,820,062 A | 1/1958 | Hillis et al. | |
| 5,977,011 A * | 11/1999 | Sauer | B01J 23/30 502/305 |
| 7,368,611 B2 * | 5/2008 | Barth | C07C 319/08 568/71 |
| 7,592,288 B2 | 9/2009 | Redlingshöfer et al. | |
| 2014/0357897 A1 | 12/2014 | Fonfe et al. | |

FOREIGN PATENT DOCUMENTS

| | | |
|---|---|---|
| CN | 103506130 A | 1/2014 |
| DE | 103 38 887 A1 | 3/2005 |
| EP | 0 832 878 A2 | 4/1998 |
| WO | WO 2013/092129 A1 | 6/2013 |

OTHER PUBLICATIONS

Extended European Search Report dated Jun. 1, 2015 in Patent Application No. 14199311.3.
European Search Report dated Apr. 8, 2016 in Patent Application No. 15 19 9713.

* cited by examiner

*Primary Examiner* — Paul A Zucker
*Assistant Examiner* — Mark Luderer
(74) *Attorney, Agent, or Firm* — Oblon, McClelland, Maier & Neustadt, L.L.P.

(57) ABSTRACT

An alkyl mercaptan is prepared by reacting an aliphatic alcohol with hydrogen sulfide in the presence of a heterogeneous catalyst at varying temperatures.

20 Claims, 1 Drawing Sheet

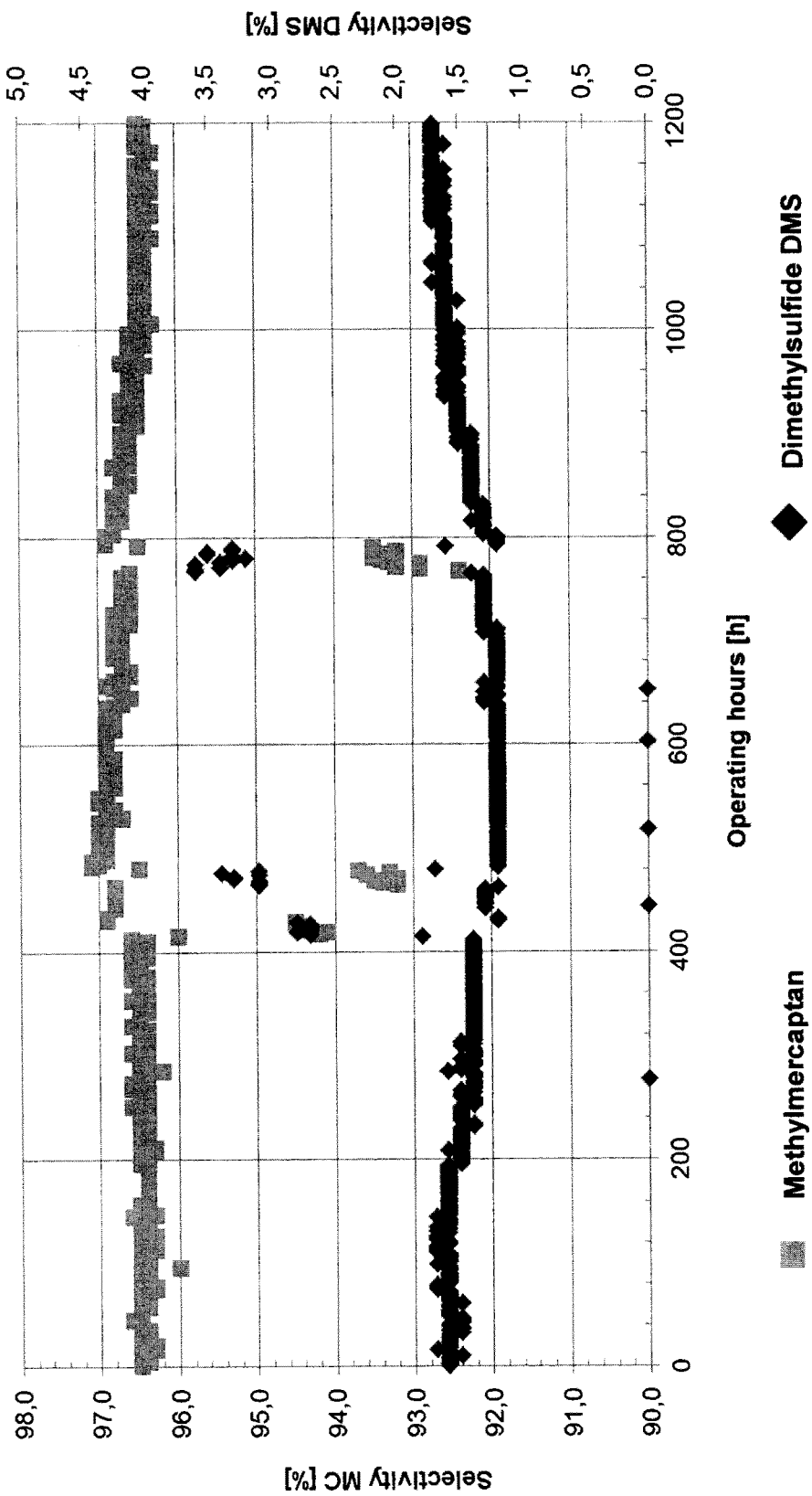

PROCESS FOR THE PREPARATION OF ALKYL MERCAPTANS

BACKGROUND OF THE INVENTION

Field of the Invention

The present invention relates to a process for the preparation of alkyl mercaptans by reacting an aliphatic alcohol with hydrogen sulfide in the presence of a heterogeneous catalyst at varying temperatures.

Discussion of the Background

Alkyl mercaptans, also referred to as alkane thiols, are organic compounds with at least one covalently bonded thiol group (—SH) as functional group. From a formalistic point of view alkyl mercaptans correspond to alkyl alcohols in which the oxygen atom is replaced with a sulfur atom. Alkyl mercaptans are useful starting or intermediate compounds in the synthesis of important organic compounds. For example, methyl mercaptan is a very important intermediate compound in the synthesis of methionine as well as of dimethyl sulfoxide or dimethyl sulfone. Nowadays low molecular weight alkyl mercaptans such as methyl mercaptan is predominantly produced by reacting an aliphatic alcohol with hydrogen sulfide in the presence of a heterogeneous catalyst, which is typically based on aluminum oxide, and this reaction is performed in the gas phase at temperatures of from 250° C. to 500° C. and pressures of from 1 bar to 25 bar. However, besides the desired alkyl mercaptan, the reaction mixture also contains non-reacted starting materials and more importantly also by-products, such as dialkyl sulfide and dialkyl ether, as well as gases, which are inert under the used reaction conditions, for example alkanes, carbon monoxide, carbon dioxide, water and nitrogen, and in the case of aliphatic alcohols other than methanol olefins are also formed as by-products. Therefore, the desired alkyl mercaptan must be separated from these compounds, which is typically done by fractional distillation. Here, the largest cost factor is in particular the energy input which is necessary for the cooling of the reaction mixture in order to condense the alkyl mercaptan.

An economically competitive process for the preparation of alkyl mercaptans thus requires to keep the energy input for the separation of the alkyl mercaptan from the non-reacted starting materials and the by-products as low as possible. In practice, it is sought to achieve this goal through the highest possible selectivity for the formation of alkyl mercaptan or the highest possible conversion rate for the aliphatic alcohol or a combination of both.

Usually, catalysts on the basis of basic aluminum oxide are used as heterogeneous catalysts in the preparation of alkyl mercaptans. The addition of an alkali metal tungstate, for example potassium or cesium tungstate, to aluminum oxide typically leads to an increase in activity and selectivity of the catalyst for the formation of the alkyl mercaptan. The added alkali metal tungstates are often also referred to as promoter or active promoter. Catalysts with such promoters are typically prepared through impregnation techniques. The amount of tungstate, based on the total weight of the catalyst, is usually up to about 25 percent by weight, as described for example in the U.S. Pat. No. 2,820,062.

The amount of the alkali metal tungstate in the catalyst can be increased to a value of 25 percent by weight, based on the total weight of the catalyst, for example through the processes described in the published patent application EP 0 832 878 A2. However, these processes are relatively complicated and time-consuming because they involve a plurality of process steps: Aluminum oxide is impregnated with a solution of the specific alkali metal tungstate multiple times and each impregnation step is followed by drying at elevated temperatures or calcination.

A further increase in selectivity is observed for catalysts with an amount of more than 25 percent by weight, based on the total weight of the catalyst, of an alkali metal tungstate. Alkali metal tungstate concentrations of more than 25 percent by weight in the final catalyst are only possible when an impregnation solution is applied to the aluminum oxide, which contains the alkali metal in question and the tungstate in stoichiometric ratio of less than 2:1, as described in the published patent application DE 103 38 887 A1. However, the observed increase in selectivity is always accompanied by a decrease in activity.

In principle, it is possible to increase the loading of the catalyst with an alkali metal tungstate to values of even more than 35 percent by weight, based on the total weight of the catalyst, by use of an impregnation solution with a non-stoichiometric ratio of the alkali metal, for example cesium, and the tungstate. However, neither a significant increase in the conversion rate of the aliphatic alcohol nor an increase in the alkyl mercaptan selectivity was observed for catalysts with such high loadings of a tungstate. Rather, it was observed that the conversion rate of the aliphatic alcohol and the selectivity for the formation of the alkyl mercaptan even decrease for catalysts which are loaded with more than 45 percent by weight of tungstate, based on the total weight of the catalyst.

At best, catalysts obtained by impregnation techniques give alkyl mercaptan selectivities of about 95%, however only with a relatively low conversion of about 80% for the aliphatic alcohol.

As far as the optimization of the catalytic system is concerned, any further improvements in the alkyl mercaptan selectivity are therefore only possible through a change of the catalytic system, for example replacing the catalysts obtained by impregnation techniques with catalysts obtained by mixing techniques. The latter can be obtained by mixing aluminum oxide particles with an oxidic tungsten compound, such as tungstic acid or an alkali tungstate, and at least one separate alkali metal compound, as described in WO 2013/092129 A1. Using this process it is possible to load catalysts with more than 45 percent by weight of a tungstate, based on the total weight of the catalyst. These catalysts give methyl mercaptan selectivities of up to 97% and methanol conversion rates of up to 98%. However, these positive effects are only observed in the initial phase of the methyl mercaptan production. Then the methanol conversion rate and the methyl mercaptan selectivity rapidly drop and at the same time the formation of dimethyl ether, which is a by-product in the methyl mercaptan production, steadily increases. It is believed that the initially high values for the methanol conversion and the methyl mercaptan selectivity are caused by catalytically active phases containing dicesium tetrathiotungstate ($W_4Cs_8S_{16}$). The drop in methyl mercaptan selectivity is believed to result from the formation of crystalline tungsten disulfide ($WS_2$), which is less selective for the formation of methyl mercaptan than $W_4Cs_8S_{16}$. It is further believed that preparing catalysts through mixing techniques, as described in WO 2013/092129 A1, only leads to a mechanic mixing of the alkali metal and tungsten, which however favors a growth of tungsten disulfide crystals. By comparison, the preparation of catalysts by impregnation techniques favors a mixing of the alkali metal and tungsten on an ionic level.

Alternatively, an improvement in the selectivity for the formation of alkyl mercaptans can also be achieved by increasing the molar ratio of hydrogen sulfide to alcohol. For example, a molar ratio of hydrogen sulfide to methanol of from 1:1 to 10:1 is usually employed in the preparation of methyl mercaptan. However, a high molar ratio of hydrogen sulfide to alkyl mercaptan necessarily results in a large excess of hydrogen sulfide in the reaction mixture and thus, the necessity to recirculate large quantities of gases back into the process. Since the recirculation of large quantities of gases requires a high energy input, the intention is to keep the excess of hydrogen sulfide as low as possible and at the same time achieve good alkyl mercaptan selectivities. In practice, the molar ratio of hydrogen sulfide to aliphatic alcohol therefore differs only slightly from 1:1. Consequently, the possibilities are limited for an improvement of conversion rates and selectivities through a modification of the molar ratio of hydrogen sulfide to alcohol.

SUMMARY OF THE INVENTION

It was therefore an objective of the present invention to provide a process for the preparation of alkyl mercaptans from aliphatic alcohols and hydrogen sulfide which gives alkyl mercaptan with a high selectivity over the whole duration of the alkyl mercaptan preparation.

It was found that this objective is solved by varying the reaction temperature during the preparation of an alkyl mercaptan between periods with a higher temperature and a lower temperature. Specifically, it was found that an increase in alkyl mercaptan selectivity is achieved when, after a period of preparing alkyl mercaptan at an initial temperature commonly used, the reaction temperature is increased to a higher temperature for a specific period, followed by decreasing the reaction temperature to a temperature.

The present invention provides in one embodiment a process for the preparation of an alkyl mercaptan, said process comprising:

reacting an aliphatic alcohol with hydrogen sulfide in the presence of a heterogeneous catalyst, and
a) starting the preparation of the alkyl mercaptan at a temperature T1 and preparing the alkyl mercaptan at the temperature T1 for a time period t1, and
b) performing temperature cycles of the number n, comprising
   b1) increasing the reaction temperature to a temperature T2 and preparing the alkyl mercaptan at the temperature T2 for a time period t2, followed by
   b2) decreasing the reaction temperature from the temperature T2 to a temperature T3 and preparing the alkyl mercaptan at the temperature T3 for a time period t3,
wherein
   the temperature T2 is always higher than the temperatures T1 and T3, and
   n is an integer larger than zero.

BRIEF DESCRIPTION OF DRAWING

The FIGURE shows the increase in the selectivity for the formation of methylmercaptan after a temperature cycle according to the process of the present invention was performed.

DETAILED DESCRIPTION OF THE INVENTION

Any ranges mentioned herein below include all values and subvalues between the lowest and highest limit of this range.

The present invention provides a process for the preparation of an alkyl mercaptan by reacting an aliphatic alcohol with hydrogen sulfide in the presence of a heterogeneous catalyst comprising the steps of
a) starting the preparation of an alkyl mercaptan at a temperature T1 and preparing the alkyl mercaptan at the temperature T1 for a time period t1, and
b) performing temperature cycles of the number n, comprising the steps of
   b1) increasing the reaction temperature to a temperature T2 and preparing the alkyl mercaptan at the temperature T2 for a time period t2, followed by
   b2) decreasing the reaction temperature from a temperature T2 to a temperature T3 and preparing the alkyl mercaptan at the temperature T3 for a time period t3,
wherein
   the temperature T2 is always higher than the temperatures T1 and T3,
and
   n is an integer larger than zero.

According to the process of the present invention at least one temperature cycle is performed, where the reaction temperature is increased in step b1) to a temperature T2 and in step b2) the temperature T2 is decreased to a temperature T3. When several temperature cycles are performed, the term reaction temperatures refers to the temperature T1 as the starting reaction temperature for the first reaction cycle and to the temperature T3 as the starting reaction temperature for the second and any further temperature cycles.

Typically, the synthesis of alkyl mercaptans from an aliphatic alcohol and hydrogen sulfide is performed at temperatures of from ca. 250° C. to ca. 500° C. Further, said synthesis is typically performed at pressures of from 1 bar to ca. 50 bar. In the context of the present invention the term ca. is used with respect to temperatures to denote all conceivable temperatures which differ by +/−10° C. from the explicitly mentioned temperature. Thus, the term ca. 250° C. comprises all integral and real number values for temperatures of from 240° C. to 260° C., in particular the integral values 240° C., 241° C., 242° C., 243° C., 244° C., 245° C., 246° C., 247° C., 248°, 249° C., 250° C., 251° C., 252° C., 253° C., 254° C., 255° C., 256° C., 257° C., 258° C., 259° C. and 260° C. Correspondingly, the term ca. 500° C. comprises all integral and real number values for temperatures of from 490° C. to 510° C., in particular the integral values 490° C., 491° C., 492° C., 493° C., 494° C., 495° C., 496° C., 497° C., 498° C., 499° C., 500° C., 501° C., 502° C., 503° C., 505° C., 506° C., 507° C., 508° C., 509° C. and 510° C. Further, in the context of the present invention the term ca. is used with respect to pressures to denote all conceivable pressures which differ by +/−5 bar from the explicitly mentioned pressure. Thus, the term ca. 50 bar comprises all integral and real number values for pressures of from 45 bar to 55 bar, in particular the integral values 45 bar, 46 bar, 47 bar, 48 bar, 49 bar, 50 bar, 51 bar, 52 bar, 53 bar, 54 bar and 55 bar.

Typically, the temperature T1, also referred to as the initial temperature T1, and the temperature T3 in step b2) in the process according to the present invention independently from each other range from ca. 250° C. to ca. 350° C. because the use of temperatures in this range already allows the synthesis of alkyl mercaptans with a selectivity of ca. 95%. The thus obtained alkyl mercaptan selectivity is essentially constant over several days or even several weeks. The term ca. 250° C. is used according to the aforementioned understanding of this term in context of the present invention. In accordance to the understanding of the term ca. in context of the present invention, the term ca. 350° C. comprises all integral and real number values for temperatures of from 340° C. to 360° C., in particular the integral values 340° C., 341° C., 342° C., 343° C., 344° C., 345° C., 346° C., 347° C., 348° C., 349° C., 350° C., 351° C., 352° C., 353° C., 354° C., 355° C., 356° C., 357° C., 358° C., 359° C. and 360° C.

In one embodiment of the present invention the temperature T1 and the temperature T3 independently from each other therefore range from 250° C.+/−10° C. to 350° C.+/−10° C.

Preference is given to a temperature T1 in the range of from ca. 270° C. to 340° C. Further preferred is a temperature T1 in the ranges of from ca. 290° C. to ca. 320° C. because temperatures in this range allow the formation of methyl mercaptan with a selectivity of even more than 95% and this value of the methyl mercaptan selectivity is essentially constant over several days or even several weeks.

During each temperature cycle the reaction temperature is increased in step b1) from the previous reaction temperature, which is either the temperature T1 or the temperature T3, to a temperature T2. According to the present invention the temperature T2 is always higher than the temperatures T1 and T3. Specifically, the temperature T2 is at least 5° C., preferably at least 10° C., 15 or 20° C. higher than each of the temperatures T1 and T3. Preferably, the temperature T2 ranges from ca. 340° C. to ca. 500° C. According to the understanding of the term ca. with respect to temperatures in context of the present invention, the term ca. 340° C. comprises all integral and real number values for temperatures of from 330° C. to 350° C., in particular the integral values 330° C., 331° C., 332° C., 333° C., 334° C., 335° C., 336° C., 337° C., 338° C., 339° C., 340° C., 341° C., 342° C., 343° C., 344° C., 345° C., 346° C., 347° C., 348° C., 349° C. and 350° C. Thus, the temperature T2 can have a lowest value of 340° C. or even less, but only under the proviso that each of the temperatures T1 and T3 is still lower than the temperature T2. For example, if the temperature T1 or T3 has a value of 340° C., then the temperature T2 must have a value of at least 345° C., preferably more than 350° C., 355° C. or 360° C. Correspondingly, the term ca. 500° C. comprises all integral and real number values for temperature of from 490° C., 491° C., 492° C., 493° C., 494° C., 495° C., 496° C., 497° C., 498° C., 499° C., 500° C., 501° C., 502° C., 503° C., 504° C., 505° C., 506° C., 507° C., 508° C., 509° C. and 510° C. Without wishing to be bound to a specific theory, it is believed that the temperature increase in step b1) leads to a reactivation of the catalyst used in the process for the preparation of an alkyl mercaptan. It is further believed that this reactivation of the catalyst is once again a sulfidation of the catalyst.

Thus, in another embodiment of the process according to the present invention the temperature T2 is at least 5° C. higher than each of the temperatures T1 and T3.

Preferably, the temperature T2 is at least 10° C., 15° C. or 20° C. higher than each of the temperatures T1 and T3.

According to the present invention the reaction temperature is decreased in step b2) from the temperature T2 to a temperature T3. Further, the temperature T1 and the temperature T3 independently from each other therefore range from ca. 250° C. to ca. 350° C.

Therefore, said temperature T3 can be higher than the temperature T1 or equal to the temperature T1. It is also possible that the temperature T3 has the same value in each temperature cycle. Alternatively, it is also possible that the temperature T3 of a temperature cycle n has a lower or higher value than the temperature T3 of a preceding temperature cycle n−1.

Thus, in another embodiment of the process according to the present invention the temperature T3 of a temperature cycle of the number n has an equal or different value compared to the temperature T3 in the preceding temperature cycle of the number n−1.

Usually, the synthesis of the alkyl mercaptan is performed under conditions which allow a conversion of ca. 90% for the aliphatic alcohol. Here, the term ca. 90% is used to denote conversions of from 85% to 95%. Thus, the term ca. 90% comprises all integral and real number values of from 85% to 95%, in particular the integral values 85%, 86%, 87%, 88%, 89%, 90%, 91%, 92%, 93%, 94% and 95%.

In addition to alkyl mercaptan selectivity, the conversion of the aliphatic alcohol is another important aspect in the preparation of alkyl mercaptans from aliphatic alcohols and hydrogen sulfide. The temperatures used in the steps a), b1) and b2) of the process according to the present invention lead to specific conversions of the alcohol in question. At higher temperatures the catalytic system used in this process is more active which thus results in an increase in the alcohol conversion and a decrease in selectivity for the formation of the respective mercaptan. In contrast, at lower temperatures the catalytic system used in the process according to the present invention is less active. This results in a decreased alcohol conversion and an increased selectivity for the formation of the alkyl mercaptan. For example, the temperature T1 in the range of from ca. 250° C. to ca. 340° C. leads to an alcohol conversion of 90+/−1% and a mercaptan selectivity of approximately 96.5%. By comparison, the temperature T2 of from ca. 340° C. to ca. 500° C. leads to an alcohol conversion of approximately 99% and at the same time gives a mercaptan selectivity of 94.5% at the most. Finally, the temperature T3, which can be lower than the temperature T1 or equal to the temperature T1 gives the mercaptan in question with a selectivity of at least 95% or even 97% at the most and leads to an alcohol conversion of 90+/−0.5%.

Therefore, the process according to the present invention preferably comprises the steps of a) starting the preparation of an alkyl mercaptan at a temperature T1 and preparing the alkyl mercaptan at the temperature T1 for a time period t1, wherein 95% at the most, preferably less than 95% or 92% of the aliphatic alcohol fed into the reaction is converted, and b) performing temperature cycle of the number n, comprising the steps of b1) increasing the reaction temperature to a temperature T2 and preparing the alkyl mercaptan at the temperature T2 for a time period t2, wherein at least 95%, preferably more than 95% or 97% and more preferably to 99% or even 100% of the aliphatic alcohol fed into the reaction is converted, followed by b2) decreasing the reaction temperature from the temperature T2 to a temperature T3 and preparing the alkyl mercaptan at the temperature T3 for a time period t3, wherein 95% at the most, preferably less than 95% or 92% of the aliphatic alcohol fed into the reaction is converted, wherein
　　the temperature T2 is always higher than the temperatures T1 and T3, and
　　n is an integer larger than zero.

Regarding the temperature T2 in different temperature cycles, the process according to the present invention is not subject to any other limitations than that the temperature T2 is always higher than the temperatures T1 and T3. It is for example possible that the temperature T2 has the same value in each temperature cycle. In this case, the temperature T2 in a temperature cycle of the number n has the same value as the temperature T2 in the preceding temperature cycle of the number n−1. This scenario is suitable for situations, where one and the same value of the temperature T2 typically leads to the same increase of selectivity for the formation of the respective alkyl mercaptan.

Therefore, in one embodiment of the process according to the present invention the temperature T2 in a temperature cycle of the number n has the same value as the temperature T2 in the preceding temperature cycle of the number n−1.

Alternatively, it is also possible to increase the temperature T2 in every consecutive temperature cycle by a specific temperature range, e.g. by a temperature range of 1° C., 2° C., 3° C., 4° C. or 5° C. relative to the temperature T2 in the preceding temperature cycle. For example, after the fifth temperature cycle (temperature cycle of the number n=5) with a temperature T2=350° C. was performed, the temperature T2 is increased to a value of e.g. 351° C., 352° C., 353° C., 345° C. or 345° C. in the next temperature cycle 6 (temperature cycle of the number n=6, i.e. temperature cycle n+1, relative to the preceding temperature cycle). This scenario is suitable for situations, where one and the same value for the temperature T2 does no longer give the same increase of selectivity for the formation of the respective alkyl mercaptan. It is believed that in cases like this only a steady increase of the temperature T2 in a consecutive temperature cycle can again lead to the desired sulfidation of the catalyst and the desired increase in selectivity for the formation of the alkyl mercaptan.

Thus, in an alternative embodiment of the process according to the present invention the temperature T2 in a temperature cycle of the number n has a higher value than the temperature T2 in the preceding temperature cycle of the number n−1.

However, it is not mandatory that in every new temperature cycle the temperature T2 increases, relative to the temperature T2 in a preceding temperature cycle. Rather, it is also possible that in a new temperature cycles the temperature T2 is only sporadically increased, relative to the temperature T2 of a preceding temperature cycle. For example, it may be necessary to increase the temperature T2 of a new temperature cycle relative to the temperature T2 of a preceding temperature cycle, where the temperature T2 of the preceding temperature cycle does no longer lead to an increased or at least recovered selectivity for the formation of the alkyl mercaptan. By comparison, it may be necessary to gradually increase the temperature T2 with every new temperature cycle, where the catalyst becomes more and more unselective during the course of the reaction. In that case it is preferred that the temperature T2 in every temperature cycle of the number n has a higher value than the temperature T2 in the preceding temperature cycle of the number n−1.

In practice, the time period t1 in step a) depends on the decrease in selectivity of the used catalyst for the formation of the alkyl mercaptan. A first temperature cycle may be performed soon after the reaction has been started or when a substantial decrease in selectivity for the formation of the alkyl mercaptan is observed, e.g. when the selectivity for the formation of alkyl mercaptan drops from ca. 96% to ca. 93%, wherein the term ca. is here used to denote deviations of +/−0.5% from the explicitly mentioned value for the selectivity. Typically, this happens after an operating time of a month. Accordingly, when the time period t1 is considered to be over, the first temperate cycle according to step b) of the process according to the present invention is performed. Typically, the time period t1 ranges from ca. 1 hour to a month, preferably ca 30 days. In the context of the present invention the term ca. is used with respect to time periods to denote all time periods which differ by +/−10% from the specifically mentioned values. Thus, the term ca. 1 hour comprises all integral and real numbers of from 1 hour−10% to 1 hour+10%. The term ca. is used with respect to days to denote all deviations by +/−10%. Thus, the term ca. 30 days comprise all integral and real number values of from 27 to 33 days, in particular the integral values 27, 28, 29, 30, 31, 32 and 33 days. The term a month here means at least one month.

Therefore, in one embodiment of the process according to the present invention the time period t1 ranges from 1 hour+/−10% to a month.

The time period t2 in step b1), in which the reaction temperature is increased to the temperature T2 and the preparation of the alkyl mercaptan is performed at said temperature, typically ranges from ca. 1 hour to ca. 50 hours. In any case, an increase in the selectivity of a catalyst, in particular of an aluminum-oxide based catalyst containing an alkali tungstate, was always observed for time period t2 in the range of from ca. 2 hours to ca. 24 hours. In the context of the present invention the term ca. is used with respect to time periods to denote all time periods which differ by +/−10% from the specifically mentioned values. Thus, the term ca. 1 hour comprises all integral and real numbers of from 1 hour−10% to 1 hour+10% and the term ca. 50 hours comprises all integral and real numbers of from 45 hours to 55 hours. Accordingly, the term ca. 6 hours comprises all integral and real number values of from 6 hours−10% to 6 hours+10% and the term ca. 24 hours comprises all integral and real number values of from 24 hours−10% to 24 hours+10%.

In another embodiment of the process according to the present invention the time period t2 ranges from 1 hour+/−10% to 50 hours+/−10%.

After completion of step b1) the preparation of an alkyl mercaptan can be performed in step b2) with an increased selectivity of up to ca. 97% for a time period t3 of from ca. 24 hours until the recharging of the reactor with a new catalyst. During this time period the selectivity for the formation of the alkyl mercaptan is permanently over 95%. In any case the preparation of an alkyl mercaptan can always be performed with an alkyl mercaptan selectivity of over 95% for a time period t3 of from ca. 24 hours until the recharging of the reactor with a new catalyst. Here, the terms ca. 24 hours is used as defined above. Typically, the reactor is recharged with a new catalyst when the old one is completely exhausted and the one catalyst cannot be refreshed again with respect to the alkyl mercaptan selectivity by performing the temperature cycles according to the present invention. However, in most cases the time t3 is already over when the selectivity for the formation of alkyl mercaptan significantly drops, for example below ca. 90%. Typically, this appears after one or more months, depending on the condition of the catalyst used. Therefore, the time period t3 is usually up to a month, i.e. at least one month.

Therefore, in one embodiment of the process according to the present invention the time period t3 is until the recharging of the reactor with a new catalyst.

In a preferred embodiment of the process according to the present invention the time period t3 is up to a month.

Typically, the industrial synthesis of alkyl mercaptans is performed in the presence of a heterogeneous catalyst. This catalyst is usually a catalyst on the basis of aluminum oxide, because aluminum oxide itself is already catalytically active in the formation of alkyl mercaptans from alkyl alcohols and hydrogen sulfide. For an improvement of the selectivity for the formation of alkyl mercaptan the aluminum oxide is usually admixed with a promoter. Said promoter is preferably an alkali metal tungstate, for example potassium tungstate ($K_2WO_4$) or cesium tungstate ($Cs_2WO_4$). Other alkali metal tungstates, which are also suitable as promoters, comprise condensed tungstates such as polytungstates or isopolytungstates, for example cesium tetratungstate ($Cs_8W_4O_{16}$), cesium heptatungstate ($Cs_6W_7O_{24}$), cesium decatungstate ($Cs_4W_{10}O_{32}$) or cesium dodecatungstate ($Cs_2W_{12}O_{40}$).

Suitable promoters are also alkali metal tungstates with a molar ratio of alkali metal to tungsten of less than 2:1, for example alkali metal tungsten bronzes. Preferably, the alkali metal tungsten bronze is an oxidic composition which corresponds to the general formula $A_xWO_y$, wherein A is at least one alkali metal selected from the group consisting of sodium, potassium, cesium, rubidium and mixtures thereof, x is equal to or larger than 0.9 and smaller than 2, i.e. x corresponds to the condition $0.9 \leq x < 2$, and y is equal to or larger than 3.4 and smaller than 4, i.e. y corresponds to the condition $3.4 \leq y < 4$. The molar ratio of an alkali metal to tungsten preferably ranges from less than 2:1 to 0.9:1, especially from 1.9:1 to 1:1. The alkali metal tungsten bronzes $K_{1.6}WO_y$, $Rb_{0.9}WO_y$, $K_{0.7}WO_y$, and $Na_{0.3}Cs_{1.1}WO_y$ are particularly suitable promoters for catalysts in the preparation of alkyl mercaptans.

Therefore, in one embodiment of the process according to the present invention the catalyst used is an aluminum oxide-based catalyst containing an alkali tungstate.

It was found that the process and in particular the temperature cycles according to the present invention give particularly good results when a catalyst is used which contains a cesium tungstate.

Thus, in a preferred embodiment of the process according to the present invention the catalyst contains a cesium tungstate.

In addition to the alkali metal tungstate, catalysts for the alkyl mercaptan production can also contain a halide, which is selected from the group consisting of fluoride, chloride, bromide, iodide and mixtures thereof. The additional presence of the halide does not affect the molar ratio of the at least one alkali metal to tungsten. Preferably, the halide containing alkali metal tungsten promoter therefore corresponds to the general formula $A_xWO_yX_z$, wherein A is at least one alkali metal selected from the group consisting of sodium, potassium, cesium, rubidium and mixtures thereof, x is equal to or larger than 0.9 and smaller than 2, i.e. x corresponds to the condition $0.9 \leq x < 2$, W is tungsten, y is equal to or larger than 3.4 and smaller than 4, i.e. y correspond to the condition $3.4 \leq y < 4$, X is at least one halide selected from the group consisting of fluoride, chloride, bromide, iodide and mixtures thereof, and z is equal to or larger than 0.01 and smaller than 12, i.e. z corresponds to the condition $0.01 \leq z < 12$. A suitable halide containing promoter is for example $Cs_2WO_4$ with added cesium fluoride, cesium chloride, cesium bromide, cesium iodide or combination thereof, in particular the combination of cesium fluoride and cesium bromide.

The common processes for the preparation of catalysts, which are suitable for the production of alkyl mercaptans, provide said catalysts in their oxidic form, which however is considered the inactive or inert form of these catalysts. Activation of said catalysts is usually caused by the presence of additional sulfur on the surface of said catalyst. The application of sulfur to the surface of the catalysts can be performed through several processes. The easiest way of applying sulfur to the surface is the direct sulfidation of the said surface by treatment with hydrogen sulfide. In principle, such a sulfidation is observed for every alkali metal tungstate containing catalysts when it is used for catalyzing the reaction of an aliphatic alcohol with hydrogen sulfide to give an alkyl mercaptan. Notwithstanding it is beneficial to sulfidize the catalysts prior to their use in the process according to the present invention because in this case the catalysts are already present in their active and thus give the highest possible turnover numbers from the very beginning of the catalyzed reaction.

Therefore, in one embodiment of the process according to the present invention the catalyst is sulfidized prior to its use in the preparation of alkyl mercaptans.

In principle, the process according to the present invention is not subject to any particular limitations regarding the aliphatic alcohol, which is reacted to the corresponding alkyl mercaptan. The only provisions regarding the aliphatic alcohol are that i) said aliphatic alcohol must not underlie any side-reactions, which did result in a decrease in yield for the desired alkyl mercaptan, ii) the aliphatic alcohol has a boiling point, which is lower than the lowest reaction temperature in the process according to the present invention, and iii) the boiling temperature of the aliphatic alcohol sufficiently differs from the boiling point of the corresponding aliphatic thiol so that a complete distillative separation from each other is possible. Apart from azeotropic mixtures, organic compounds having differences in boiling temperatures of approximately 10 K can be easily and completely separated from one another by means of distillation. In general, aliphatic alcohols with from one to three carbon atoms can be easily separated from their corresponding aliphatic alkyl thiols by means of distillation. For example the boiling points of methanol (64.9° C.) and methyl mercaptan (6.2° C.) differ by more than 58° C. The longer the respective alkyl chains are, the closer are the boiling points of aliphatic alcohols and their corresponding thiols. For example, the boiling points of ethanol (78° C.) and ethyl mercaptan (35.0° C.) differ by 42° C. and the boiling points of n-propanol (82° C.) and iso-propanol (2-propanol) (97° C.) only differ ca. 30° C. or 29° C. from the boiling points of their corresponding alkyl mercaptans. Notwithstanding these alcohols can still be easily separated from their corresponding thiols. By comparison, the boiling temperatures of tert-butanol and tert-butyl mercaptan are only 18° C. away from each other, and the boiling temperatures of n-butanol and iso-butanol are almost identical to the boiling temperatures of the corresponding thiols.

In one embodiment of the process according to the present invention the aliphatic alcohol therefore is a $C_1$ to $C_3$ alcohol.

In a preferred embodiment of the process according to the present invention the aliphatic alcohol is methanol, ethanol, n-propanol, iso-propanol or tert-butanol.

The economically most relevant alkyl mercaptan obtained or obtainable by the process according to the present invention is methyl mercaptan.

Therefore, in a further preferred embodiment of the process according to the present invention the aliphatic alcohol is methanol.

The present invention is further explained by the following items:

1. Process for the preparation of an alkyl mercaptan by reacting an aliphatic alcohol with hydrogen sulfide in the presence of a heterogeneous catalyst comprising the steps of
   a) starting the preparation of an alkyl mercaptan at a temperature T1 and preparing the alkyl mercaptan at the temperature T1 for a time period t1, and
   b) performing temperature cycles of the number n, comprising the steps of
      b1) increasing the reaction temperature to a temperature T2 and preparing the alkyl mercaptan at the temperature T2 for a time period t2, followed by
      b2) decreasing the reaction temperature from the temperature T2 to a temperature T3 and preparing the alkyl mercaptan at the temperature T3 for a time period t3,
   wherein
      the temperature T2 is always higher than the temperatures T1 and T3, and
      n is an integer larger than zero.
2. Process according to item 1, wherein the temperature T1 and the temperature T3 independently from each other range from 250° C.+/−10° C. to 350° C.+/−10° C.
3. Process according to item 1 or 2, wherein the temperature T2 is at least 5° C. higher than each of the temperatures T1 and T3.
4. Process according to any of items 1 to 3, wherein the temperature T3 of a temperature cycle of the number n has an equal or a different value compared to the temperature T3 in the preceding temperature cycle of the number n−1.
5. Process according to any of items 1 to 4, wherein the temperature T2 in a temperature cycle of the number n has the same value as the temperature T2 in the preceding temperature cycle of the number n−1.
6. Process according to any of items 1 to 4, wherein the temperature T2 in a temperature cycle of the number n has a higher value than the temperature T2 in the preceding temperature cycle of the number n−1.
7. Process according to any of items 1 to 6, wherein the time period t1 ranges from 1 hour+/−10% to a month.
8. Process according to item 7, wherein the time period t2 ranges from 1 hour+/−10% to 50 hours+/−10%.
9. Process according to any of items 1 to 8, wherein the time period t3 is until the recharging of the reactor with a new catalyst.
10. Process according to item 9, wherein the time period t3 is up to a month.
11. Process according to any of items 1 to 10, wherein an aluminum oxide-based catalyst containing an alkali tungstate is used.
12. Process according to item 11, wherein the catalyst contains a cesium tungstate.
13. Process according to any of items 1 to 12, wherein the catalyst is sulfidized prior to its use in the preparation of alkyl mercaptans.
14. Process according to any of items 1 to 13, wherein the aliphatic alcohol is a $C_1$-$C_3$ alcohol.
15. Process according to item 14, wherein the aliphatic alcohol is methanol, ethanol, n-propanol, iso-propanol or tert-butanol.

FIGURE

The FIGURE shows the increase in the selectivity for the formation of methylmercaptan after a temperature cycle according to the process of the present invention was performed.

Having generally described this invention, a further understanding can be obtained by reference to certain specific examples which are provided herein for purposes of illustration only, and are not intended to be limiting unless otherwise specified.

EXAMPLE

The preparation of methyl mercaptan from methanol and hydrogen sulphide was performed over an aluminum oxide-based catalyst containing cesium tungstate as promoter in a common tube reactor with a length of the catalyst bed of 294 cm and a total catalyst mass of 1,760 grams for a period of 59 days.

The reaction conditions and the experimental results are summarized in the Table 1 below.

European patent application No. 14199311.3 filed Dec. 19, 2014, is incorporated herein by reference.

Numerous modifications and variations on the present invention are possible in light of the above teachings. It is therefore to be understood that within the scope of the appended claims, the invention may be practiced otherwise than as specifically described herein.

TABLE 1

Summary of the reaction details over a period of approximately 60 days.

| Date | Time | Temperature salt bath [° C.] | Conversion MeOH [%] | Selectivity [%] | | | | | | |
|------|------|------------------------------|---------------------|------|------|------|------|------|------|--------|
|      |      |                              |                     | MC   | DMS  | DME  | $CO_2$ | CO   | DMDS | Methan |
| 11.05. | 09:17:00 | 300.0 | 90.6 | 96.5 | 1.6 | 1.5 | 0.1 | 01. | 0.2 | 0.1 |
| 29.05. | 10:30:00 | 312.0 | 90.4 | 96.4 | 1.4 | 1.6 | 0.2 | 0.1 | 0.2 | 0.1 |
| 30.05. | 17:04:00 | 351.0 | 98.8 | 94.2 | 2.7 | 0.8 | 1.1 | 0.2 | 0.2 | 0.8 |
| 30.05. | 04:55:00 | 351.0 | 98.8 | 94.5 | 2.8 | 0.8 | 0.9 | 0.2 | 0.2 | 0.7 |
| 30.05. | 07:42:00 | 312.0 | 88.3 | 96.9 | 1.2 | 1.4 | 0.1 | 0.1 | 0.2 | 0.1 |
| 30.05. | 23:50:00 | 314.0 | 90.3 | 96.8 | 1.3 | 1.4 | 0.1 | 0.1 | 0.2 | 0.1 |
| 31.05. | 14:46:00 | 314.0 | 90.6 | 96.8 | 1.2 | 1.4 | 0.1 | 0.1 | 0.2 | 0.1 |
| 31.05. | 19:01:00 | 360.0 | 99.2 | 93.4 | 3.1 | 0.6 | 1.3 | 0.2 | 0.2 | 1.1 |
| 01.06. | 06:39:00 | 360.0 | 99.1 | 93.7 | 3.1 | 0.6 | 1.2 | 0.2 | 0.2 | 1.0 |
| 01.06. | 10:55:00 | 314.0 | 89.6 | 97.1 | 1.1 | 1.3 | 0.1 | 0.1 | 0.2 | 0.1 |
| 11.06. | 12:33:00 | 310.5 | 90.3 | 96.7 | 1.2 | 1.5 | 0.2 | 0.1 | 0.2 | 0.1 |

TABLE 1-continued

Summary of the reaction details over a period of approximately 60 days.

| Date | Time | Temperature salt bath [° C.] | Conversion MeOH [%] | Selectivity [%] | | | | | | |
|---|---|---|---|---|---|---|---|---|---|---|
| | | | | MC | DMS | DME | CO$_2$ | CO | DMDS | Methan |
| 14.06. | 03:16:00 | 311.0 | 88.4 | 96.7 | 1.3 | 1.4 | 0.2 | 0.1 | 0.2 | 0.1 |
| 14.06. | 09:09:00 | 360.0 | 99.1 | 92.8 | 3.6 | 0.6 | 1.4 | 0.3 | 0.2 | 0.9 |
| 15.06. | 06:59:00 | 360.0 | 99.0 | 93.5 | 3.3 | 0.6 | 1.2 | 0.3 | 0.2 | 0.8 |
| 15.06. | 10:59:00 | 312.0 | 88.3 | 96.9 | 1.2 | 1.3 | 0.1 | 0.1 | 0.3 | 0.1 |
| 11.07. | 18:33:00 | 316.0 | 89.0 | 96.4 | 1.7 | 1.2 | 0.2 | 0.1 | 0.3 | 0.1 |
| 11.07. | 19:00:00 | 360.0 | 99.0 | 93.5 | 3.3 | 0.6 | 1.2 | 0.3 | 0.2 | 0.8 |
| 11.07. | 01:52:00 | 360.0 | 99.0 | 93.5 | 3.3 | 0.6 | 1.2 | 0.3 | 0.2 | 0.8 |
| 12.07. | 01:52:00 | 316.0 | 87.2 | 96.5 | 1.6 | 1.2 | 0.2 | 0.1 | 0.3 | 0.1 |
| 13.07 | 14.53:00 | 320.5 | 89.6 | 96.3 | 1.8 | 1.2 | 0.2 | 0.1 | 0.3 | 0.1 |
| 13.07. | 17:04:00 | 360.0 | 98.8 | 92.9 | 4.0 | 0.6 | 1.3 | 0.2 | 0.3 | 0.7 |
| 14.07 | 05:00:00 | 360.0 | 98.8 | 92.9 | 4.0 | 0.6 | 1.2 | 0.2 | 0.3 | 0.7 |
| 14.07. | 07:01:00 | 320.5 | 88.1 | 96.5 | 1.7 | 1.1 | 0.2 | 0.1 | 0.3 | 0.1 |
| 18.07. | 15:04:00 | 322.5 | 89.6 | 96.3 | 1.8 | 1.1 | 0.2 | 0.1 | 0.3 | 0.1 |

The invention claimed is:

1. A process for preparing an alkyl mercaptan, the process comprising:
reacting an aliphatic alcohol with hydrogen sulfide in the presence of a heterogeneous catalyst, and
a) starting the preparation of the alkyl mercaptan at a temperature T1 and preparing the alkyl mercaptan at the temperature T1 for a time period t1, and
b) performing temperature cycles of the number n, comprising
b1) increasing the reaction temperature to a temperature T2 and preparing the alkyl mercaptan at the temperature T2 for a time period t2, followed by
b2) decreasing the reaction temperature from the temperature T2 to a temperature T3 and preparing the alkyl mercaptan at the temperature T3 for a time period t3,
wherein
the temperature T2 is always higher than the temperatures T1 and T3,
and
n is an integer larger than zero.

2. The process according to claim 1, wherein the temperature T1 and the temperature T3 independently from each other range from 250° C.+/−10° C. to 350° C.+/−10° C.

3. The process according to claim 1, wherein the temperature T2 is at least 5° C. higher than each of the temperatures T1 and T3.

4. The process according to claim 1, wherein the temperature T3 of a temperature cycle of the number n has an equal or a different value compared to the temperature T3 in the preceding temperature cycle of the number n−1.

5. The process according to claim 1, wherein the temperature T2 in a temperature cycle of the number n has the same value as the temperature T2 in the preceding temperature cycle of the number n−1.

6. The process according to claim 1, wherein the temperature T2 in a temperature cycle of the number n has a higher value than the temperature T2 in the preceding temperature cycle of the number n−1.

7. The process according to claim 1, wherein the time period t1 ranges from 1 hour+/−10% to a month.

8. The process according to claim 7, wherein the time period t2 ranges from 1 hour+/−10% to 50 hours+/−10%.

9. The process according to claim 1, wherein the time period t3 is until the recharging of the reactor with a new catalyst.

10. The process according to claim 9, wherein the time period t3 is up to a month.

11. The process according to claim 1, wherein an aluminum oxide-based catalyst containing an alkali tungstate is used.

12. The process according to claim 11, wherein the catalyst contains a cesium tungstate.

13. The process according to claim 1, wherein the catalyst is sulfidized prior to its use in the preparation of alkyl mercaptans.

14. The process according to claim 1, wherein the aliphatic alcohol is a $C_1$-$C_3$ alcohol.

15. The process according to claim 14, wherein the aliphatic alcohol is methanol, ethanol, n-propanol, iso-propanol or tert-butanol.

16. The process according to claim 1, wherein methyl mercaptan is prepared from methanol and hydrogen sulphide over an aluminum oxide-based catalyst containing cesium tungstate as promoter.

17. The process according to claim 2, wherein the temperature T2 is at least 5° C. higher than each of the temperatures T1 and T3.

18. The process according to claim 2, wherein the temperature T3 of a temperature cycle of the number n has an equal or a different value compared to the temperature T3 in the preceding temperature cycle of the number n−1.

19. The process according to claim 2, wherein the temperature T2 in a temperature cycle of the number n has the same value as the temperature T2 in the preceding temperature cycle of the number n−1.

20. The process according to claim 2, wherein the temperature T2 in a temperature cycle of the number n has a higher value than the temperature T2 in the preceding temperature cycle of the number n−1.

* * * * *